(12) United States Patent  
Seki et al.

(10) Patent No.: US 11,083,914 B2
(45) Date of Patent: Aug. 10, 2021

(54) ULTRASONIC TREATMENT DEVICE

(71) Applicant: SOUND WAVE INNOVATION CO., LTD., Tokyo (JP)

(72) Inventors: Yoshinori Seki, Tokyo (JP); Kazunori Itani, Tokyo (JP); Hiroaki Shimokawa, Miyagi (JP); Hiroshi Kanai, Miyagi (JP)

(73) Assignee: Sound Wave Innovation Co., Ltd., Tokyo (JP)

( * ) Notice: Subject to any disclaimer, the term of this patent is extended or adjusted under 35 U.S.C. 154(b) by 1275 days.

(21) Appl. No.: 15/037,111

(22) PCT Filed: Nov. 17, 2014

(86) PCT No.: PCT/JP2014/080365
§ 371 (c)(1),
(2) Date: May 17, 2016

(87) PCT Pub. No.: WO2015/072566
PCT Pub. Date: May 21, 2015

(65) Prior Publication Data
US 2016/0296767 A1 Oct. 13, 2016

(30) Foreign Application Priority Data
Nov. 18, 2013 (JP) .............................. JP2013-237707

(51) Int. Cl.
A61N 7/00 (2006.01)
A61B 8/00 (2006.01)
(Continued)

(52) U.S. Cl.
CPC .............. *A61N 7/00* (2013.01); *A61B 8/0883* (2013.01); *A61B 8/5207* (2013.01); *A61B 8/54* (2013.01);
(Continued)

(58) Field of Classification Search
CPC .... A61N 7/00; A61N 7/02; A61N 2017/2205; A61N 2017/0004; A61N 2017/0052;
(Continued)

(56) References Cited

U.S. PATENT DOCUMENTS 8,099,154 B1  1/2012  Wess et al.
2006/0241522 A1  10/2006  Chandraratna
2013/0261508 A1  10/2013  Shimokawa et al.

FOREIGN PATENT DOCUMENTS

JP  62047358 A  3/1987
JP  07231893 A  9/1995
(Continued)

OTHER PUBLICATIONS

K. Hanawa et al., The 46th Meeting of Tohoku Branch of Japanese Society for medical nad Biological Engineering Nov. 17, 2012, Sendai Japan (English translation). (Year: 2012).*
(Continued)

Primary Examiner — Boniface N Nganga
(74) Attorney, Agent, or Firm — Baker Botts, L.L.P.

(57) ABSTRACT

A probe (10) transmits and receives diagnostic ultrasound and therapeutic ultrasound. A transmission unit (12) forms a transmission beam of the therapeutic ultrasound having a higher wave number than the diagnostic ultrasound and scans the transmission beam of the therapeutic ultrasound in a therapeutic region set inside a diagnostic region by controlling the probe (10). Since the therapeutic ultrasound having a higher wave number than the diagnostic ultrasound is used, the therapeutic effect is higher than when using a therapeutic ultrasound having a similar wave number to the diagnostic ultrasound, and since the transmission beam of the therapeutic ultrasound is scanned in the therapeutic region, the therapeutic effect is higher than when the transmission beam of the therapeutic ultrasound is not scanned.

9 Claims, 7 Drawing Sheets

(51) Int. Cl.
*A61B 8/08* (2006.01)
*A61N 7/02* (2006.01)
*A61B 17/22* (2006.01)

(52) U.S. Cl.
CPC ...... *A61N 7/02* (2013.01); *A61B 2017/22005* (2013.01); *A61N 2007/0004* (2013.01); *A61N 2007/0052* (2013.01); *A61N 2007/0073* (2013.01); *A61N 2007/0082* (2013.01)

(58) Field of Classification Search
CPC .... A61N 2017/0073; A61N 2017/0082; A61B 8/54; A61B 8/5207; A61B 8/0883
See application file for complete search history.

(56) References Cited

FOREIGN PATENT DOCUMENTS

| | | |
|---|---|---|
| JP | 3058645 B2 | 4/2000 |
| JP | 2005304918 A | 11/2005 |
| JP | 2011015732 A | 1/2011 |
| JP | 2013055984 A | 3/2013 |
| WO | 2012077219 A1 | 6/2012 |

OTHER PUBLICATIONS

J.C. Lacefield, "Diagnostic Radiological Physics" Chapter 12 Physics of Ultrasound (Year: 2014).*
Japanese Office Action for Japanese Patent Application No. 2015-547815, dated Jul. 17, 2018, 7 pages.
K. Hanawa, et al., "Low-Intensity Pulsed Ultrasound Induces Angiogenesis and Ameliorates Left Ventricular Dysfunction in a Porcine Model of Chronic Myocardial Ischemia", The 16th Annual Meeting of the Japanese Heart Failure Society, Nov. 30, 2012, Sendai, Japan.
K. Hanawa, et al., The 46th Meeting of Tohoku Branch of Japanese Society for Medical and Biological Engineering, Nov. 17, 2012, Sendai, Japan.

* cited by examiner

ULTRASONIC TREATMENT DEVICE

TECHNICAL FIELD

The present invention relates to an ultrasonic treatment device.

BACKGROUND

In treatment of an ischemic tissue, such as, for example, treatment of ischemic heart disease, invasive treatments by surgical operations have been carried out so far. This treatment method is highly invasive to and imposes a significant burden on the patient.

Accordingly, in recent years, a method of treating ischemic tissues using shock waves has been developed. It is a method of treating, for example, a cardiac muscle tissue which has been damaged due to stenosis or occlusion of a part of the coronary arteries of the heart, by applying weak shock waves to the tissue. A known therapeutic effect is that when an ischemic tissue is irradiated with shock waves, regeneration of new blood vessels is promoted at that irradiated site. This treatment method is non-invasive and places only a small burden on the patient. As an example of a device that implements such a treatment method, for example, a device disclosed in Patent Document 1 is known. This device is an application of a calculus-crushing device, and applies to the affected part shock waves with a weaker output than the calculus-crushing device.

Because the device of the type disclosed in Patent Document 1 cannot obtain an in-vivo image using a shock wave irradiation head, an ultrasonic diagnostic device for identifying an irradiation site, etc. must be provided separately. However, because a probe of the ultrasonic diagnostic device cannot be placed in the same position as the shock wave irradiation head, a diagnostic image of the ultrasonic diagnostic device is obtained from a viewpoint and a gaze direction different from that of the shock wave irradiation head.

In addition, because the shock wave irradiation head is relatively large, for example, in the treatment of the heart, shock waves are applied not only to the cardiac muscle to be treated but also to other tissues, such as a rib and a pulmonary tissue. In this case, because the rib and the pulmonary tissue have acoustic impedance values that are very different from those of living soft tissues, shock waves cause reflection and scattering at a boundary with the living soft tissues, and shock waves reaching the cardiac muscle or the like which is a treatment object are reduced, while shock waves reaching the tissues other than the treatment object are increased.

In view of such circumstances, the applicant of the present application proposes, in Patent Document 2, an ultrasonic treatment device that minimizes irradiation of ultrasound to sites other than a treatment site.

CITATION LIST

Patent Literature

Patent Document 1: JP 3058645 B
Patent Document 2: JP 2011-15732 A

SUMMARY

Technical Problem

In view of the above-described background art, the inventors of the present application have continued research and development for further improvement of the ultrasonic treatment device.

Solution to Problem

The present invention has been achieved in the process of that research and development, and its purpose is to provide an ultrasonic treatment device having higher therapeutic effect than that of the prior art.

A preferable ultrasonic treatment device that fulfills the above-described purpose has a probe that transmits and receives ultrasound, a transmission unit that scans a transmission beam of diagnostic ultrasound in a diagnostic region by controlling the probe, a receiving unit that obtains a received signal of diagnostic ultrasound along a receiving beam corresponding to the transmission beam of diagnostic ultrasound, and an image-forming unit that forms an ultrasound image of the diagnostic region based on the received signal of diagnostic ultrasound, and in this device, the transmission unit forms a transmission beam of therapeutic ultrasound by controlling the probe, and scans the transmission beam of therapeutic ultrasound within a treatment region which is set to be in the diagnostic region.

In the above device, diagnostic ultrasound has a wavenumber and an irradiation intensity that are a similar level to ultrasound used in, for example, diagnosis in a conventional general ultrasonic diagnostic device, and diagnostic ultrasound is transmitted and received, for example, using a vibration element of a conventional general ultrasonic diagnostic device. In contrast, therapeutic ultrasound is desirably has a larger wavenumber than diagnostic ultrasound. Therapeutic ultrasound may have an irradiation intensity that is a similar level to diagnostic ultrasound, and therapeutic ultrasound can be transmitted and received using a vibration element for transmitting and receiving diagnostic ultrasound. As a matter of course, a vibration element for transmitting and receiving diagnostic ultrasound and a vibration element for transmitting and receiving therapeutic ultrasound may be provided separately.

With the above device, because therapeutic ultrasound having a larger wavenumber than that of diagnostic ultrasound is used, the therapeutic effect is enhanced as compared to the case where therapeutic ultrasound having a wavenumber that is of a similar level to diagnostic ultrasound is used. For example, if the wavenumber diagnostic ultrasound is one or two cycles or so, the wavenumber of therapeutic ultrasound is set to be more than three cycles. In order to further enhance the therapeutic effect, the wavenumber of therapeutic ultrasound is desirable to be more than, for example, six cycles, and is selected from 16 cycles, 32 cycles, 48 cycles, and 64 cycles, for example. According to the experimental results, the highest therapeutic effect is expected to be obtained from 32 cycles, and therefore, it is particularly desirable to set the wavenumber of therapeutic ultrasound to 32 cycles. As a matter of course, as the high therapeutic effect is expected from wavenumbers that are a similar level to 32 cycles, the wavenumber of therapeutic ultrasound is not strictly limited to 32 cycles, and it may be set to a wavenumber that is a similar level to 32 cycles. Wavenumbers that are of a similar level to 32 cycles include, for example, 16 to 48 cycles, and, desirably, are 24 to 40 cycles, but are not limited to these examples.

In addition, with the above device, because a transmission beam of therapeutic ultrasound is scanned within the treatment region, the therapeutic effect is enhanced as compared to the case where the transmission beam of therapeutic ultrasound is not scanned. Modes of scanning the transmission beam of therapeutic ultrasound include not only continuous scanning by shifting an angle or a position of the transmission beam for each line but also discrete scanning by changing an angle or a position of the transmission beam over a plurality of lines regularly or irregularly. According to the experimental results, although there is improvement in the treatment site (e.g. ischemic tissue) when it is irradiated with therapeutic ultrasound having a larger wavenumber than diagnostic ultrasound, a normal site (e.g. normal tissue) is not affected significantly. Therefore, even if the treatment sites and the normal sites are mixed in the treatment region, therapeutic ultrasound is transmitted over e entire area of the treatment region while suppressing the effect on the normal site, thereby treating the treatment sites over the entire region of the treatment region. In other words, by scanning the transmission beam of therapeutic ultrasound within the treatment region, wide area treatment is enabled, and the therapeutic effect of the entire treatment region is enhanced.

In a desirable specific example, for example, the transmission unit control probe so as to transmit therapeutic ultrasound having a wavenumber of 32 cycles.

In a desirable specific example, the ultrasonic treatment device has a diagnostic mode that uses diagnostic ultrasound and a treatment mode that uses therapeutic ultrasound. In the treatment mode, the transmission unit scans the transmission beam of therapeutic ultrasound within the treatment region; the receiving unit obtains a received signal of therapeutic ultrasound from the inside of the treatment region along the receiving beam corresponding to the transmission beam of therapeutic ultrasound; and the image-forming unit forms an ultrasonic image of the treatment region based on the received signal of therapeutic ultrasound.

In a desirable specific example, the ultrasonic treatment device has a diagnostic mode that uses diagnostic ultrasound and a treatment mode that uses therapeutic ultrasound. In the treatment mode, the transmission unit scans the transmission beam of therapeutic ultrasound within the treatment region an as to change radiation pressure of therapeutic ultrasound periodically, and causes a treatment site to swing using changing radiation pressure.

Advantageous Effects of Invention

The present invention provides an ultrasonic treatment device having higher therapeutic effect than in the prior art. For example, according to a preferable embodiment of the present invention, because therapeutic ultrasound having a larger wavenumber than that of diagnostic ultrasound is used, the therapeutic effect is enhanced as compared to the case where therapeutic ultrasound having a wavenumber that is of a similar level to diagnostic ultrasound is used. In addition, for example, according to a preferable embodiment of the present invention, because the transmission beam of therapeutic ultrasound is scanned within the treatment region, the therapeutic effect is enhanced as compared to the case where the transmission beam of therapeutic ultrasound is not scanned.

DESCRIPTION OF EMBODIMENTS

Figure 1:
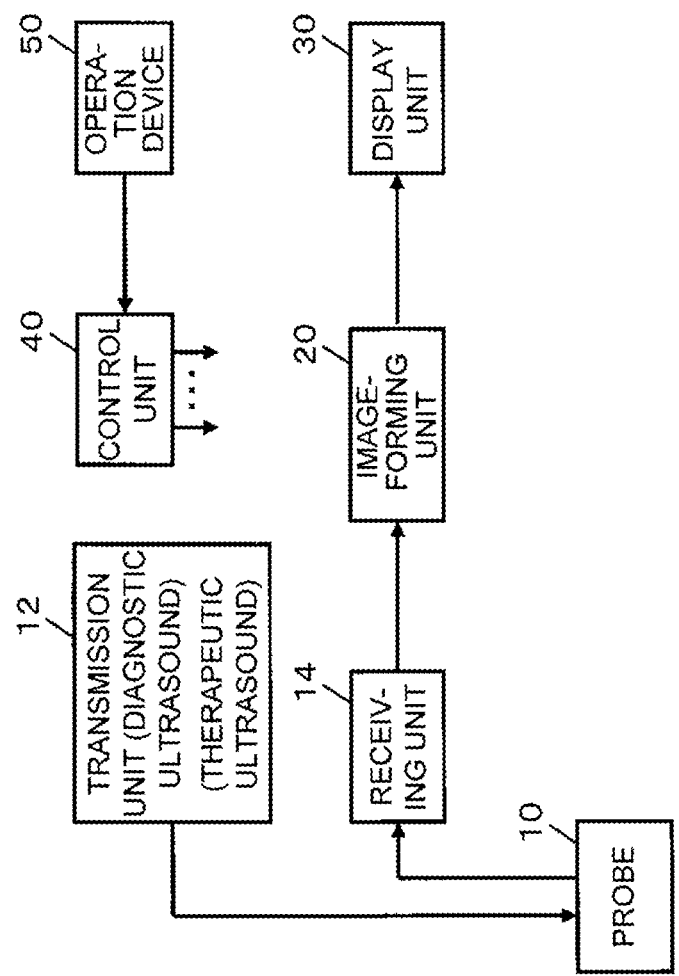
FIG. 1 shows a diagram showing the entire configuration of a preferable ultrasonic treatment device in an embodiment of the present invention.

FIG. 1 shows the entire configuration diagram of a preferable ultrasonic treatment device 100 in implementation of the present invention. The ultrasonic treatment device 100 is suitable for treatment of ischemic tissues, for example, and an example of a preferable treatment object is the heart. As a matter of course, treatment objects of the ultrasonic treatment device 100 are not limited to the heart, and for example, vessels and organs other than the heart may also be treatment objects. The ultrasonic treatment device 100 uses diagnostic ultrasound and therapeutic ultrasound.

A probe 10 has a plurality of vibration elements (not shown) for transmitting and receiving diagnostic ultrasound and therapeutic ultrasound. The plurality of vibration elements may be in any element arrangement according to, such as, for example, a convex scan type, a sector scan type, and a linear scan type, or any element arrangement for a two-dimensional image (tomographic image) and for a three-dimensional image. Although it is desirable that each of the plurality of vibration elements provided in the probe 10 can transmit and receive both diagnostic ultrasound and therapeutic ultrasound, vibration elements for transmitting and receiving diagnostic ultrasound and vibration elements for transmitting and receiving therapeutic ultrasound may be provided separately.

A transmission unit 12 outputs transmission signals to the plurality of vibration elements provided in the probe 10, to thereby control the probe 10. The transmission unit 12 scans the transmission beam of diagnostic ultrasound within a diagnostic region by controlling the probe 10. The transmission unit 12 also scans a transmission beam of therapeutic ultrasound within a treatment region by controlling the probe 10. In other words, the transmission unit 12 has the function as a transmission beam former. Specific scanning processing by the transmission unit 12 will be described in detail later.

A receiving unit 14 forms a receiving beam, for example, by performing phasing addition processing on the plurality of wave receiving signals obtained from the plurality of vibration elements provided in the probe 10, thereby obtaining received signals along the receiving beam. In other words, the receiving unit 14 has the function as a receiving beam former. The receiving unit 14 forms a receiving beam corresponding to the transmission beam of diagnostic ultrasound, to thereby obtain received signals of diagnostic ultrasound from the inside of the diagnostic region. The receiving unit 14 also forms a receiving beam corresponding to the transmission beam of therapeutic ultrasound, to thereby obtain received signals of therapeutic ultrasound from the inside of the treatment region.

An image-forming unit 20 forms an ultrasonic image of the diagnostic region based on the received signals of diagnostic ultrasound. The image-forming unit 20 also forms an ultrasonic image of the treatment region based on the received signals of therapeutic ultrasound. A preferable specific example of an ultrasonic image is a B-mode image obtained by known B-mode imaging processing. The image-forming unit 20 may also form, as the ultrasonic image, a three-dimensional ultrasonic image or a color Doppler image, for example. The ultrasonic image formed in the image-forming unit 20 is displayed on a display unit 30.

A control unit 40 controls the inside the ultrasonic treatment device 100 intensively. An operation device 50 is a device that receives the user's operation, and an instruction received by the operation device 50 from the user is transmitted to the control unit 40 and is reflected on the control of the inside of the ultrasonic treatment device 100.

Each of the transmission unit 12, the receiving unit 14, and the image-forming unit 20 is implemented using hardware, such as, for example, a processor and an electronic circuit. In addition, a preferable specific example of the display unit 30 is, for example, a liquid crystal display, etc. Further, the operation device 50 is composed of at least some of, for example, a mouse, track ball, keyboard, touch panel, other switches, etc. Still further, the control unit 40 is composed of, for example, hardware such as a CPU having a calculation function, and when the hardware works in cooperation with software (program) that defines operation of the hardware, the functions of the control unit 40 are implemented.

The entire configuration of the ultrasonic treatment device 100 is as described above. Next, the functions and the like that are implemented by the ultrasonic treatment device 100 will be described in detail. In the following description, the components (parts) that are shown in FIG. 1 use the same reference numerals as in FIG. 1.

Figure 2:
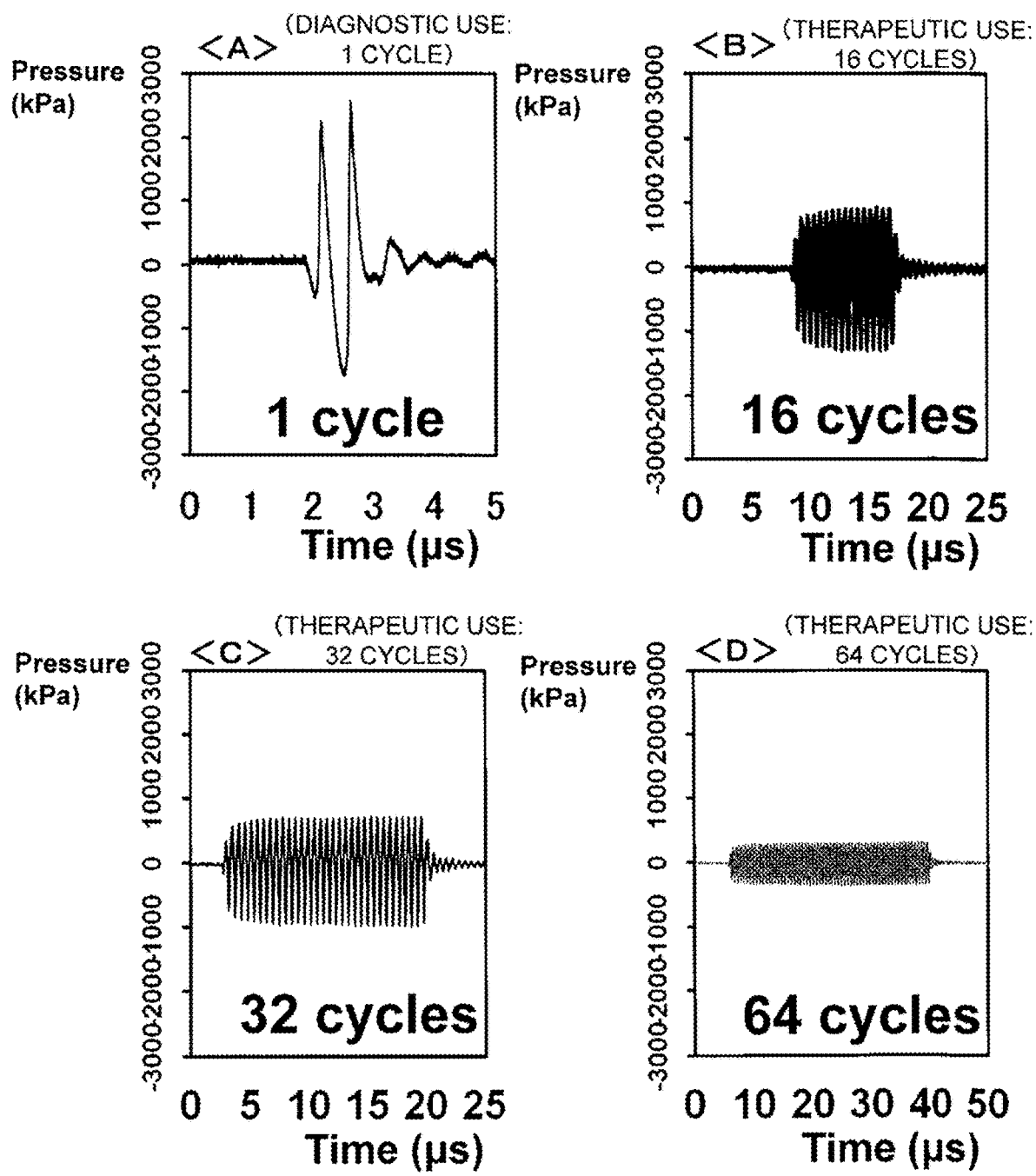
FIG. 2 shows a diagram showing specific examples of diagnostic ultrasound and therapeutic ultrasound.

FIG. 2 shows a diagram showing specific examples of diagnostic ultrasound and therapeutic ultrasound. FIG. 2 shows waveforms of diagnostic ultrasound and therapeutic ultrasound transmitted in the ultrasonic treatment device 100 in FIG. 1.

Diagnostic ultrasound has the wavenumber and the irradiation intensity that area similar level to those of ultrasound used in diagnosis, for example, by conventionally-known general ultrasonic diagnostic devices. Ultrasound used in diagnosis by a general ultrasonic diagnostic device has, typically, one or two cycles or so. Therefore, in the ultrasonic treatment device 100 in FIG. 1, the wavenumber of diagnostic ultrasound is, for example, one or two or so. FIG. 2<A> shows, as a specific example of diagnostic ultrasound, a waveform having a wavenumber of one (one cycle). As diagnostic ultrasound, for example, waveforms having two to six cycles or so may also be used.

Meanwhile, therapeutic ultrasound has long bursting waves having larger wavenumbers than diagnostic ultrasound. It is desirable that the wavenumber of therapeutic ultrasound is, for example, greater than six cycles, and more specifically, it is selected from, for example, 16 cycles, 32 cycles, 48 cycles, and 64 cycles. FIG. 2<B> shows, as a specific example of therapeutic ultrasound, a waveform having a wavenumber of 16 (16 cycles); FIG. 2<C> shows, as a specific example of therapeutic ultrasound, a waveform having wavenumber of 32 (32 cycles); and FIG. 2<D> shows, as a specific example of therapeutic ultrasound, a waveform having wavenumber of 64 (64 cycles).

Figure 3:
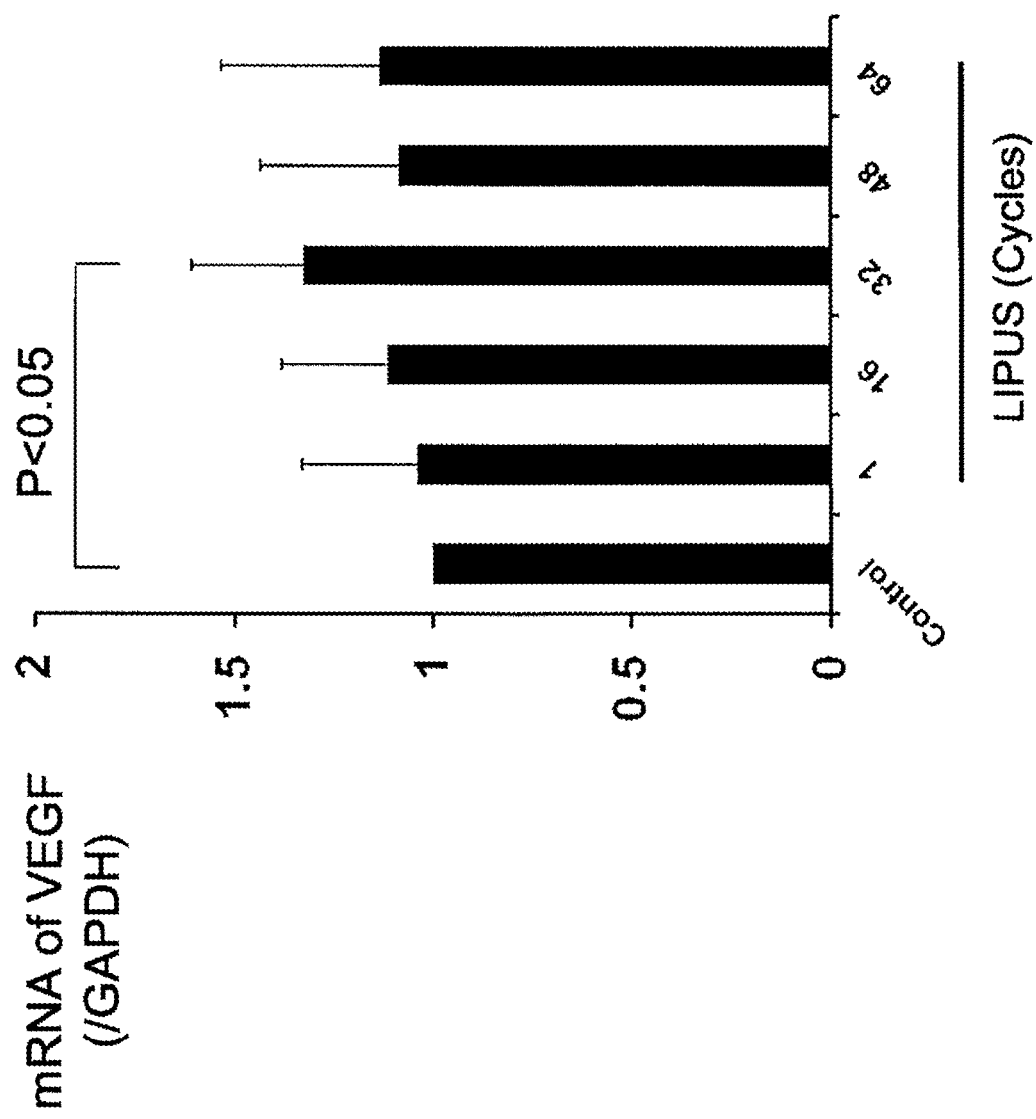
FIG. 3 shows a diagram showing experimental results relating to expression of vascular endothelial growth factors.

FIG. 3 shows a diagram showing experimental results relating to expression of vascular endothelial growth factors. FIG. 3 shows expression of vascular endothelial growth factors (VEGF) (vertical axis) when wavenumbers of therapeutic ultrasound are set to be 1 (1 cycle), 16 (16 cycles), 32 (32 cycles), 48 (48 cycles), and 64 (64 cycles), and the expression is highest in the case of 32 cycles. In other words, according to these experimental results, the therapeutic effect is highest in the ischemic tissue when therapeutic ultrasound has a wavenumber of 32 cycles. Therefore, in the ultrasonic treatment device 100 in FIG. 1, therapeutic ultrasound having a wavenumber of, for example, 32 cycles is used.

Figure 4:
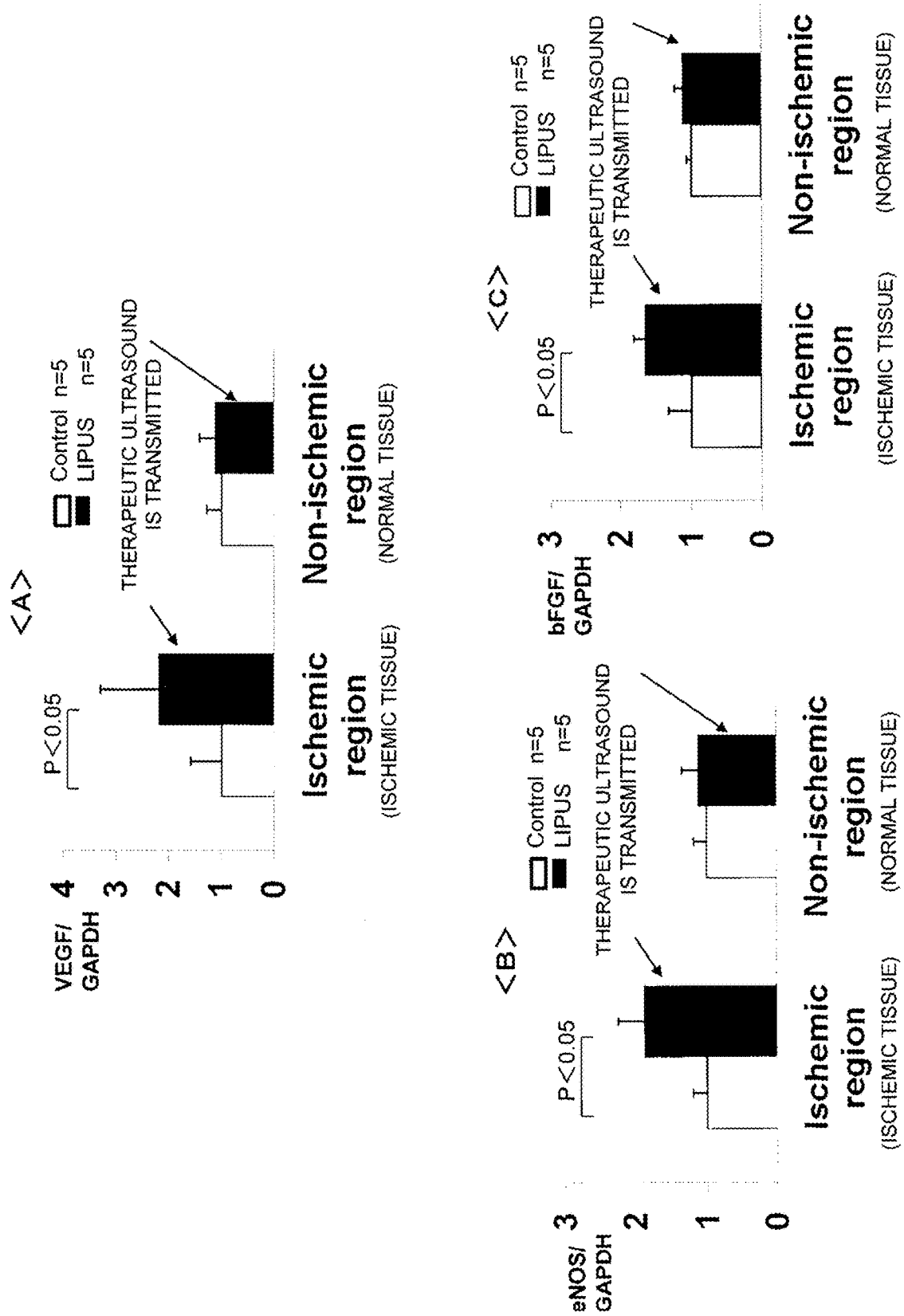
FIG. 4 shows a diagram showing experimental results relating to impact of therapeutic ultrasound on tissues.

FIG. 4 shows a diagram showing experimental results relating to impact of therapeutic ultrasound on tissues. FIG. 4<A> shows experimental results relating to expression of vascular endothelial growth factors (VEGF); FIG. 4<B> shows experimental results relating to expression of endothelial nitric oxide synthase (eNOS); and FIG. 4<C> shows experimental results relating to expression of basic fibroblast growth factors (bFGF). FIGS. 4<A> to <C> show expression amounts of the factors obtained when therapeutic ultrasound is transmitted to both of the ischemic tissue and a normal tissue.

As shown in FIG. 4, although, in all the factors from <A> to <C>, the expression is promoted in the ischemic tissue by transmitting therapeutic ultrasound, while expression is suppressed in the normal tissue. In other words, by using therapeutic ultrasound, the therapeutic effect on the ischemic tissue appears, while the impact on the normal tissue is suppressed.

Figure 5:
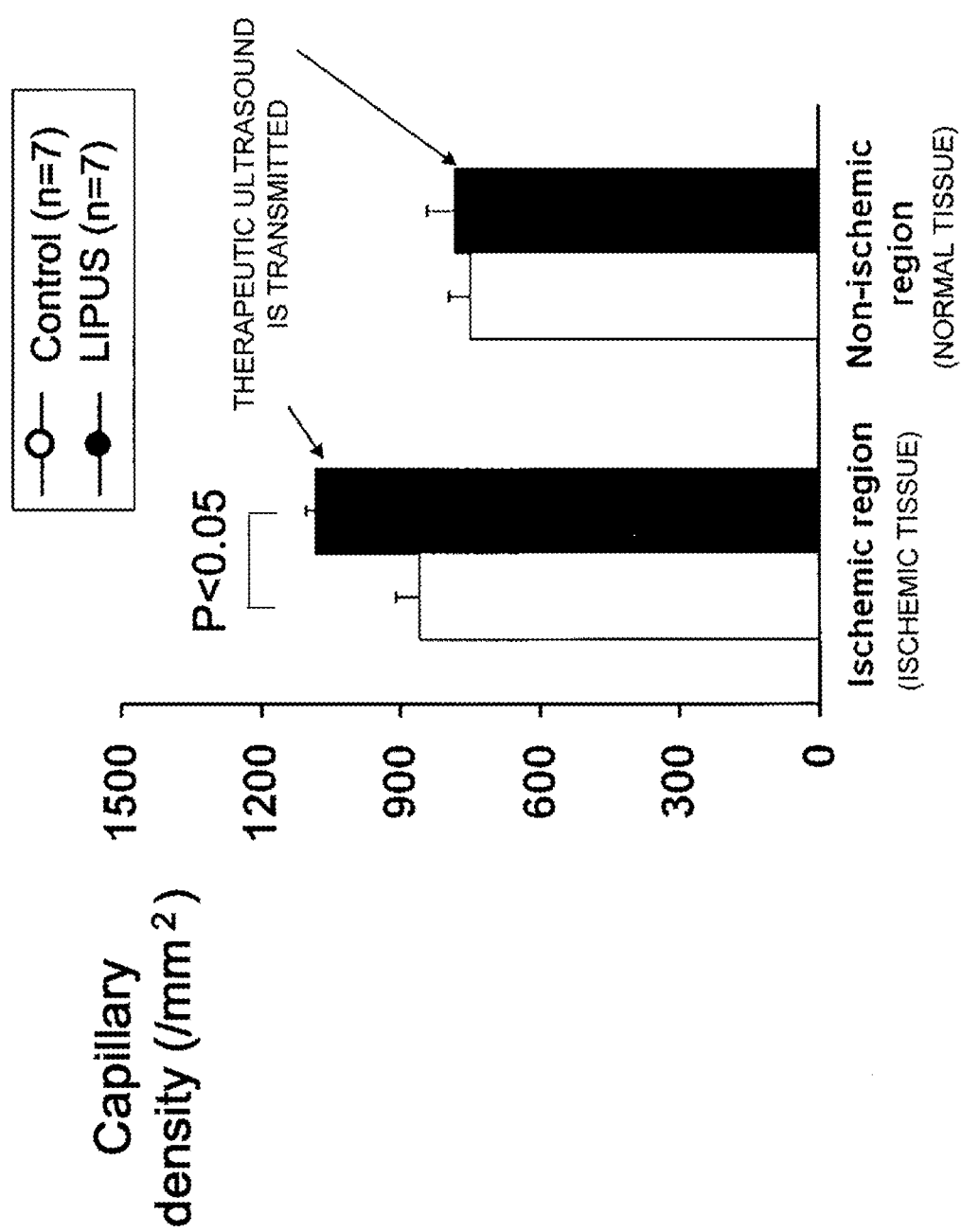
FIG. 5 shows a diagram showing experimental results relating to the capillary density.

FIG. 5 shows a diagram showing experimental results relating to capillary density. FIG. 5 shows the capillary density obtained when therapeutic ultrasound is transmitted to both of the ischemic tissue and the normal tissue. As shown in FIG. 5, by transmitting therapeutic ultrasound, the capillary density is increased in the ischemic tissue, while the increase in the capillary density is suppressed in the normal tissue. In other words, by using therapeutic ultrasound, the capillary density is enhanced only in the ischemic site.

Therefore, even if the treatment sites (ischemic tissue) and the normal sites (normal tissue) are mixed in the treatment region, the ultrasonic treatment device 100 in FIG. 1 treats the treatment sites over the entire area of the treatment region, suppressing the effect on the normal sites by scanning the transmission beam of therapeutic ultrasound over the entire area of the treatment region.

Figure 6:
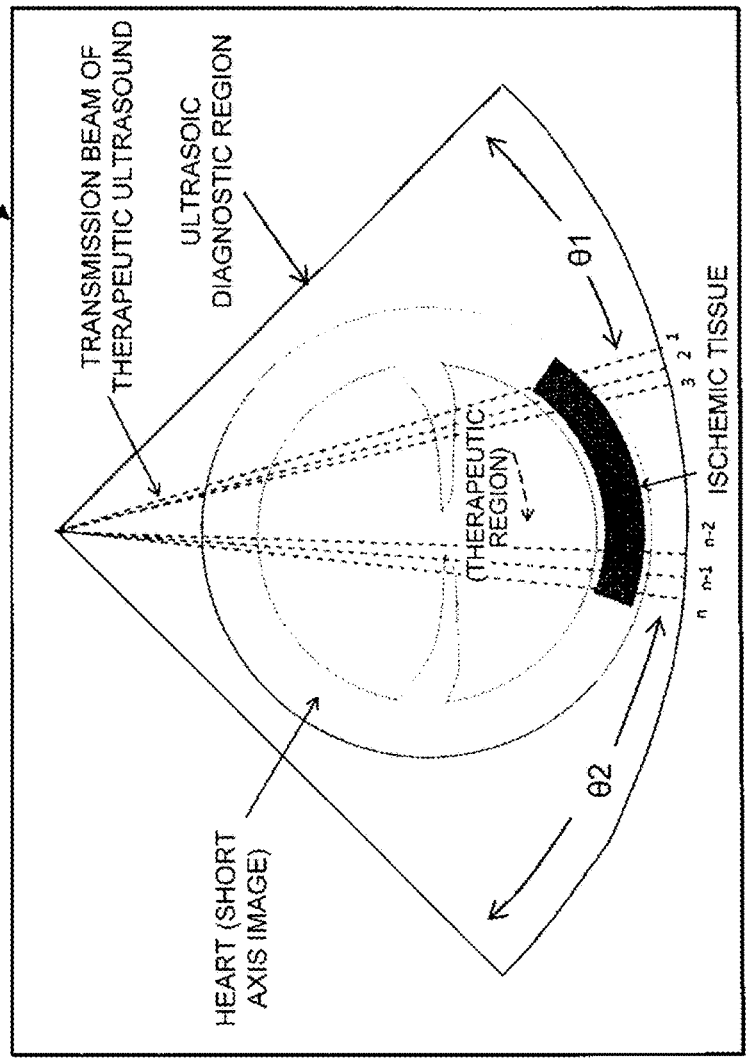
FIG. 6 shows a diagram showing a specific example of scanning of therapeutic ultrasound.
Figure 6:
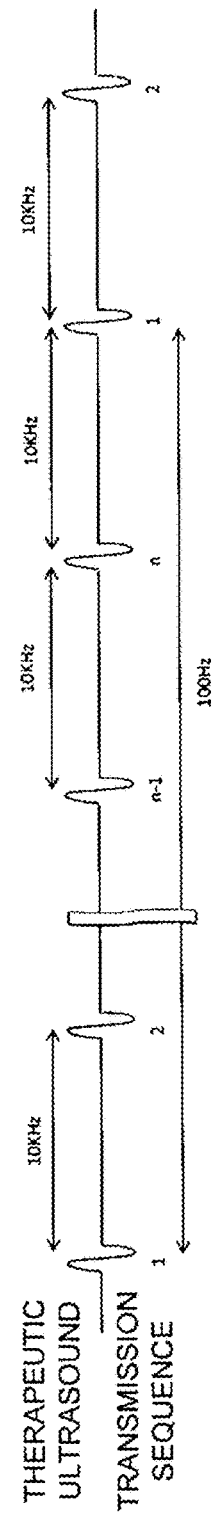

FIG. 6 shows a diagram showing a specific example of scanning of therapeutic ultrasound. FIG. 6 shows a specific example of the case in which the ischemic tissue in the cardiac muscle of the heart is treated, and FIG. 6 shows a display image 32 that is displayed on the display unit 3. The display image 32 includes an ultrasonic image of the treatment region including the heart; that is, a B-mode image of a cardiac short axis (short-axis image).

The B-mode image of the cardiac short axis is formed by known B-mode image forming processing via diagnostic ultrasound. More specifically, the transmission unit 12 scans the transmission beam of diagnostic ultrasound within the diagnostic region, and the receiving unit 14 collects received signals from the diagnostic region along a receiving beam corresponding to the transmission beam. The image-forming unit 20 forms a B-mode image of the diagnostic region based on the received signals.

Once the B-mode image of the diagnostic region is formed, the treatment region is set so as to include the ischemic tissue of the cardiac muscle, which is the treatment site. For example, as shown in FIG. 6, an angle θ1 of a right side boundary line and an angle θ2 of a left side boundary line are set within the diagnostic region, and the region between the set right side boundary line and the left side boundary line is the treatment region. The user (person who provides treatment, such as a medical doctor) of the ultrasonic treatment device 100 operates the operation device 50 such as a track ball, while looking at the display image 32 showing the cardiac short axis image, to thereby adjust the angle θ1 of the right side boundary line and the angle θ2 of the left side boundary line and set the treatment region to be within the diagnostic region.

Once the treatment region is set, the transmission unit 12 scans a transmission beam of therapeutic ultrasound within the treatment region, and conducts treatment of the ischemic tissue. The transmission unit 12 scans the transmission beam of therapeutic ultrasound, for example, as shown in FIG. 6, in the order from line 1 corresponding to the right side boundary line, lines 2, 3, 4 . . . until line n corresponding to the left side boundary line. The transmission unit 12 may also perform scanning so as to shift the lines of transmission beam over a plurality of lines regularly or irregularly, in place of performing scanning so as to shift the lines of the transmission beam one by one.

Desirably, a focal point of the transmission beam of therapeutic ultrasound (focus depth) is set at the depth where the ischemic tissue exists. For example, the user operates the operation device 50, while looking at the display image 32, thereby setting the focus depth of therapeutic ultrasound. A treatment range of the treatment region (pulse repetition period of therapeutic ultrasound) may also be the same as a diagnostic range of the diagnostic region (pulse repetition period of diagnostic ultrasound), or the treatment range of the treatment region may also be adjusted in accordance with the focus depth of therapeutic ultrasound.

It is also known that tissue is displaced by radiation force of ultrasound which is generated when ultrasound is transmitted to the tissue. Therefore, the transmission unit 12 scans a transmission beam of therapeutic ultrasound within the treatment region so as to change radiation pressure of therapeutic ultrasound periodically, and causes the treatment site to swing using changing radiation pressure. The therapeutic effect is further increased by transmitting therapeutic ultrasound while causing the treatment site to swing.

The range in which the tissue vibrates is determined by the repetition frequency of ultrasound and the speed of a transverse wave. Because the speed of the transverse wave in vivo is about 1 to 10 m/sec, for example, if the speed of the transverse wave in the tissue is 1 m/sec, and if ultrasound is transmitted repeatedly at the period of 100 Hz, the range having a length of 10 mm near the focal point of ultrasound is vibrated more effectively. By determining the repetition frequency of therapeutic ultrasound according to the size of the tissue to be treated and the speed of the transverse wave, the therapeutic effect additionally including the effect of mechanical vibration by the radiation force can be expected.

FIG. 6 shows a specific example of a transmission sequence of therapeutic ultrasound that is preferable for vibration by radiation force. In the specific example shown in FIG. 6, the transmission beams of therapeutic ultrasound are scanned in the order from lines 1, 2, 3, 4 . . . until line n. Assuming that the pulse repetition frequency (PRF) between adjacent beams is 10 kHz, and that the number of beams n is 100, the period in which therapeutic ultrasound is applied to the same tissue position becomes 100 Hz, and the tissue position can be vibrated effectively. The treatment site may also be vibrated by ultrasound for radiation which generates radiation force, in place of therapeutic ultrasound.

Figure 7:
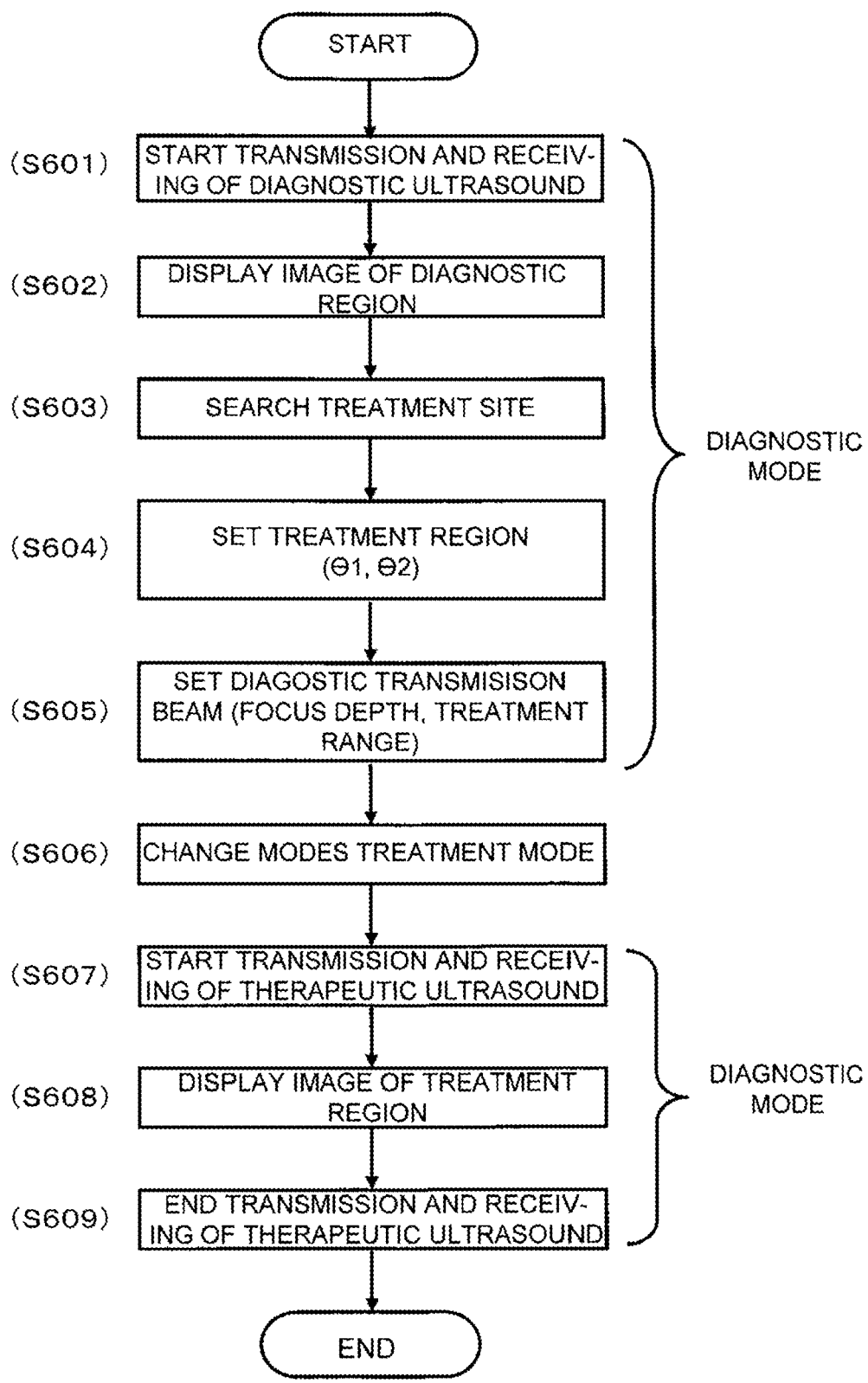
FIG. 7 shows a flowchart showing an operation example of the ultrasonic treatment device of FIG. 1.

FIG. 7 shows a flowchart showing a treatment example by the ultrasonic treatment device of FIG. 1. First, a diagnostic mode using diagnostic ultrasound is performed before a treatment mode using therapeutic ultrasound. More specifically, transmission and receiving of diagnostic ultrasound is started (S601), and an ultrasonic image of the diagnostic region relating to a subject including the treatment site is displayed (S602).

The user (person who provides treatment, such as a medical doctor) of the ultrasonic treatment device 100 moves the probe 10 manually when necessary, looking at an ultrasonic image displayed on the display unit 30 (e.g. the cardiac short axis image shown in FIG. 6), to thereby search the treatment site in the subject (S603). Once the treatment site has been searched, the user operates the operation device 50 and sets the treatment region (by way of example, the angle θ1 and the angle θ2 shown in FIG. 6) so that the treatment site shown in the ultrasonic image is included in the treatment region (S604). If the ultrasonic image is a three-dimensional image, for example, a two-dimensional treatment region (angle θ1 and angle θ2) may be set in any two-dimensional plane, and a two-dimensional treatment region (angle θ3 and angle θ4) may be set in a two-dimensional plane intersecting with (for example, orthogonal to) the two-dimensional plane, thereby setting a three-dimensional stereoscopic treatment region based on these two-dimensional treatment regions. As a matter of course, methods for setting the three-dimensional treatment region are not limited to the above specific example. The user further sets the focus depth relating to the transmission beam of therapeutic ultrasound so that therapeutic ultrasound is transmitted to the treatment site effectively, and sets a treatment range of the treatment region to which therapeutic ultrasound is transmitted (S605).

After setting for treatment is ended, the ultrasonic treatment device 100 is switched from the diagnostic mode to the treatment mode (S606), and transmission of therapeutic ultrasound is started. A transmission beam of therapeutic ultrasound is scanned within the treatment region (S607), and treatment is conducted by therapeutic ultrasound. Desirably, the probe 10 is fixed using, for example, a jig at any timing after search for the treatment site (S603) is performed and before transmission of therapeutic ultrasound is started (S607).

Moreover, while the transmission beam of therapeutic ultrasound is scanned within the treatment region, and treatment is conducted, the receiving unit 14 forms a receiving beam corresponding to the transmission beam of therapeutic ultrasound and obtains received signals of therapeutic ultrasound from the inside of the treatment region. Then, the image forming unit 20 forms an ultrasound image (e.g. B-mode image) of the treatment region based on the received signals of therapeutic ultrasound, and the formed ultrasound image is displayed on the displayed unit 30 (S608). Thus, the user can confirm a treatment state from the ultrasonic image of the treatment region. The user can confirm, for example, whether or not therapeutic ultrasound is being transmitted to the treatment region.

Thus, after treatment is performed on the treatment region, which has been set in S604, for example, for about 20 minutes, transmission of therapeutic ultrasound is ended (S609), and treatment for the treatment region is ended. If there is a need to set a plurality of treatment regions in the subject, the flowchart in FIG. 7 is implemented for each treatment region, for example.

Although the preferable embodiment of the present invention has been described, the above-described embodiment is merely an example in all respects, and should not be deemed to limit the present invention. The present invention includes various variations without departing from the spirit of the present invention.

REFERENCE SIGNS LIST 10 probe, 12 transmission unit, 14 receiving unit, 20 image-forming unit, 30 display unit, 40 control unit, 50 operation device, 100 ultrasonic treatment device.

The invention claimed is:

1. An ultrasonic treatment device comprising:
   a probe that transmits and receives ultrasound;
   a transmission unit that scans a transmission beam of diagnostic ultrasound in a diagnostic region by controlling the probe;
   a receiving unit that obtains a received signal of diagnostic ultrasound along a receiving beam corresponding to the transmission beam of diagnostic ultrasound; and
   an image-forming unit that forms an ultrasound image of the diagnostic region based on the received signal of diagnostic ultrasound, wherein
   the transmission unit forms a transmission beam of therapeutic ultrasound by controlling the probe, scans the transmission beam of therapeutic ultrasound within a treatment region which is set to be in the diagnostic region;
   and the transmission unit scans the transmission beam of therapeutic ultrasound within the treatment region so as to change a radiation pressure of therapeutic ultrasound periodically, and causes a treatment site to oscillate using changing radiation pressure,
   wherein the transmission unit controls the probe so as to transmit therapeutic ultrasound having a wavenumber of 6 to 64 cycles.

2. The ultrasonic treatment device according to claim 1, wherein
   the transmission unit controls the probe so as to transmit therapeutic ultrasound having a wavenumber of 32 cycles.

3. The ultrasonic treatment device according to claim 2, wherein
   the transmission unit scans the transmission beam of therapeutic ultrasound in the treatment region including an ischemic tissue.

4. The ultrasonic treatment device according to claim 3, wherein
   the transmission unit sets a focal point of the transmission beam of therapeutic ultrasound at a depth of the ischemic tissue.

5. The ultrasonic treatment device according to claim 1, wherein
   the transmission unit scans the transmission beam of therapeutic ultrasound in the treatment region including an ischemic tissue.

6. The ultrasonic treatment device according to claim 5, wherein
   the transmission unit sets a focal point of the transmission beam of therapeutic ultrasound at a depth of the ischemic tissue.

7. The ultrasonic treatment device according to claim 6, wherein
   the transmission unit forms a transmission beam of the therapeutic ultrasound transmitted at a repetition frequency according to a size of a tissue to be treated and a speed of a transverse wave of the tissue.

8. The ultrasonic treatment device according to claim 5, wherein
   the transmission unit forms a transmission beam of the therapeutic ultrasound transmitted at a repetition frequency according to a size of a tissue to be treated and a speed of a transverse wave of the tissue.

9. The ultrasonic treatment device according to claim 1, wherein
   the transmission unit forms a transmission beam of the therapeutic ultrasound transmitted at a repetition frequency according to a size of a tissue to be treated and a speed of a transverse wave of the tissue.

* * * * *